(12) United States Patent
Slawson et al.

(10) Patent No.: US 6,390,625 B1
(45) Date of Patent: May 21, 2002

(54) FOCUSING MECHANISM

(75) Inventors: Steven R. Slawson, Camillus; Ronald A. Hauptli, Warners; Chris R. Roberts; Allan I. Krauter, both of Skaneateles; Ervin Goldfain, Syracuse, all of NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/774,726

(22) Filed: Jan. 31, 2001

(51) Int. Cl.$^7$ .................................. A61B 3/10
(52) U.S. Cl. ........................................ 351/216
(58) Field of Search ........................ 351/205, 206, 351/216, 218, 233, 236; 359/410, 411, 412, 416, 425, 414; 396/85; 600/181

(56) References Cited

U.S. PATENT DOCUMENTS 5,062,698 A * 11/1991 Funathu ..................... 359/414
6,065,837 A * 5/2000 Goldfain et al. ............ 351/205
6,110,106 A * 8/2000 MacKinnon et al. ........ 600/181

* cited by examiner

Primary Examiner—George Manuel
(74) Attorney, Agent, or Firm—Wall Marjama & Bilinsk LLP

(57) ABSTRACT

A focusing mechanism for an optical instrument includes an eyepiece having at least one lens element retained within an eyepiece housing, a stationary carrier for retaining the eyepiece, and a rotatable thumb wheel. A pair of levers operatively connect the eyepiece housing with the rotatable thumb wheel, the thumb wheel including corresponding pairs of cam channels on either side for receiving one end of a corresponding lever, the remaining end of each lever engaging the eyepiece housing, wherein rotational movement of the thumb wheel produces axial movement of the eyepiece relative to said carrier.

35 Claims, 4 Drawing Sheets

FOCUSING MECHANISM

FIELD OF THE INVENTION

The invention relates to the field of focusing mechanisms, and more particularly to a focusing mechanism for an ophthalmoscope or other suitable optical instrument.

BACKGROUND OF THE INVENTION

As is well known, ophthalmoscopes are medical diagnostic instruments which are used for examining the eyes. An indirect small pupil ophthalmoscope, for example, as described in U.S. Pat. No. 6,065,837, includes an instrument housing which retains a light source as well as a set of lens modules and an eyepiece. The eyepiece should be adjustably movable in order to adjust the position of the eyepiece focal plane relative to the image of the retina of a patient's eye being viewed to compensate for the refractive error of either the patient or the physician.

Several prior art mechanisms are known for axially adjusting the position of an eyepiece. Each, however, is relatively complex in design requiring many different components or extreme dimensional tolerancing in order to function adequately. Simpler designs requiring a manual focus adjustment member do not appear to relieve any backlash, which makes axial adjustment difficult or produces lateral or other loads on the eyepiece or the mechanism that cause axial adjustment to be imprecise.

SUMMARY OF THE INVENTION

It is a primary object of the present invention to improve the field of optical instruments.

It is a further primary object of the present invention to improve the operation of the focusing mechanism of an optical instrument such as an ophthalmoscope.

It is yet a further primary object of the present invention to produce a manual focusing mechanism for an optical instrument which provides the correct ratio of thumbwheel motion to eyepiece motion while minimizing backlash in the focusing mechanism as well as lateral loads induced on the eyepiece.

Therefore and according to a preferred aspect of the present invention, there is described a focusing mechanism comprising:
- a eyepiece having at least one lens element retained within an eyepiece housing;
- a stationary carrier for retaining said eyepiece;
- a movable thumb wheel operatively connected to said stationary carrier; and
- at least one lever operatively connecting said eyepiece housing and said thumb wheel, said thumb wheel including a cam channel for receiving a first end of said at least one lever, and in which an opposing second end of said at least one lever engages said eyepiece housing, such that rotational movement of said thumb wheel produces corresponding axial movement of the eyepiece relative to the stationary carrier.

Preferably, a pair of levers interconnect the thumb wheel with the eyepiece, the levers each having first ends which engage a corresponding spiral cam channel that is provided on each side of the thumb wheel. The eyepiece includes a channel which receives an opposing second end of each corresponding lever. As the thumb wheel rotates, the engagement members of each of the levers track within the spiral cam channels. Based upon a hinged mount of the levers to the stationary carrier, the levers are caused to pivot, thereby producing effectively axial motion of the remaining ends of the lever and controlled axial motion of the eyepiece. According to this embodiment, the pivoting axis of the levers and the mounting axis of the thumb wheel are each substantially perpendicular to the optical axis of the instrument, but do not intersect with the optical axis of the instrument. Moreover, second or top ends of the levers are preferably substantially aligned with the centerline (e.g. the optical axis of the instrument) of the eyepiece housing.

More preferably, each of the first ends of the levers include split bosses or fingers which more adequately insure simultaneous engagement with each side of the spiral channel of the thumb wheel. The engagement of the split bosses thereby reduces backlash transmitted to the eyepiece as a result of the rotational motion of the thumb wheel. The split fingers could also be provided at the opposing ends of the levers; that is, the ends in contact with a receiving channel of the eyepiece housing, if desired, to produce a similar benefit.

In the meantime, the eyepiece is retained in radial biasing engagement within the stationary carrier. According to a preferred embodiment, the carrier includes at least one integral spring finger which imparts a radial load on the eyepiece when installed in the carrier. This radial load effectively retains the eyepiece while permitting the eyepiece to track axially along guide surfaces which are provided on the interior of the stationary carrier.

According to another preferred aspect of the present invention, there is described an optical instrument comprising:
- an instrument housing;
- an eyepiece;
- a stationary carrier disposed within said instrument housing and sized for retaining said eyepiece;
- a rotatable thumb wheel operatively connected to said stationary carrier; and
- at least one lever operatively connecting said eyepiece and said rotatable thumb wheel, said thumb wheel including a cam channel for receiving a first end of said at least one lever, and in which an opposing second end of said at least one lever engages said eyepiece such that rotational movement of said thumb wheel produces corresponding axial movement of the eyepiece relative to the stationary carrier.

Preferably, a pair of levers operatively interconnect the eyepiece and the thumb wheel, the levers being hingably attached to the stationary carrier. First ends of the levers are retained within spiral cam channels of the thumb wheel, with each lever being disposed on an opposite side of the thumb wheel. Second ends of the levers engage the eyepiece. As the thumb wheel rotates, the levers track the spiral cam channels, producing hinged motion of the levers and axial movement of the eyepiece.

Preferably, the first ends of the levers are split, thereby defining split fingers which simultaneously engage the sides of each spiral cam channel. The eyepiece is effectively biased radially within the stationary carrier into guide surfaces defined in the interior of the carrier which facilitates controlled axial movement based on a given rotation of the thumb wheel. More preferably, stops are provided at ends of the spiral cam channel which engage the stationary carrier so as to impart loads onto the levers or the eyepiece at the ends of travel. Alternately or in combination with the above, the second or top ends of the levers can also be spilt to provide simultaneous engagement with the sides of each receiving channel of the eyepiece housing. Still more preferably, the top ends of each of the levers are substantially aligned with the centerline of the eyepiece housing; that is, with the optical axis of the instrument.

According to yet another preferred aspect of the invention, a method of axially adjusting an eyepiece of an optical instrument relative to an optical axis of said instrument is provided. The method includes the steps of:

retaining an eyepiece housing in a stationary carrier, said stationary carrier being operatively connected to a rotatable thumb wheel;

linking a first end of said at least one lever to said rotatable thumb wheel and a second end of said at least one lever to said eyepiece housing, said at least one lever being hingably attached to said stationary carrier; and rotating said rotatable thumb wheel, causing the first end of said at least one lever to track a spiral channel of said thumb wheel, pivoting said at least one lever about the hingable attachment to said stationary carrier to produce axial movement of said eyepiece.

An advantage of the present invention is that the described focusing mechanism permits thumb wheel rotation in order to effectively move the eyepiece without producing incidental lateral or side loads and with a minimum of backlash.

Another advantage of the present invention is that the above focusing mechanism is relatively simple to manufacture; and does not require excessive dimensional tolerancing; for example, the spiral channel of the rotatable thumb wheel. As a result, the above focusing mechanism is also more inexpensive to manufacture and maintain than other prior known mechanisms.

Yet another advantage provided by the present invention is that the above described mechanism can be utilized in literally any optical instrument requiring an eyepiece.

These and other objects, features, and advantages will be readily apparent from the following Detailed Description which should be read in conjunction with the accompanying drawings.

DETAILED DESCRIPTION

Figure 1:
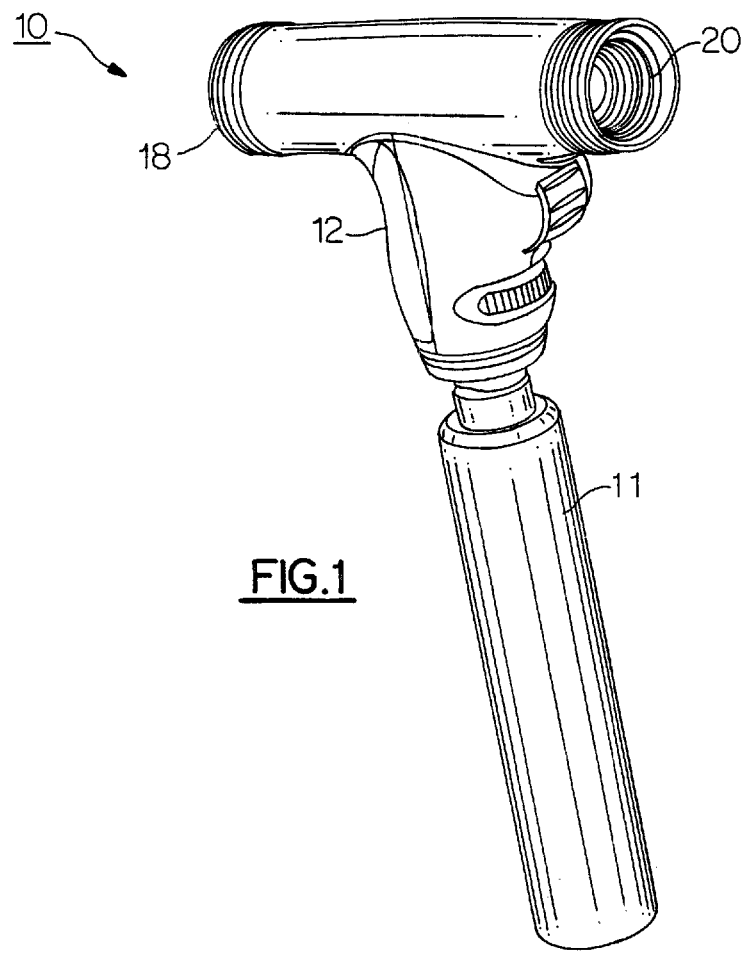
FIG. 1 is a perspective view of an optical instrument utilizing a focusing mechanism according to the present invention.
Figure 2:
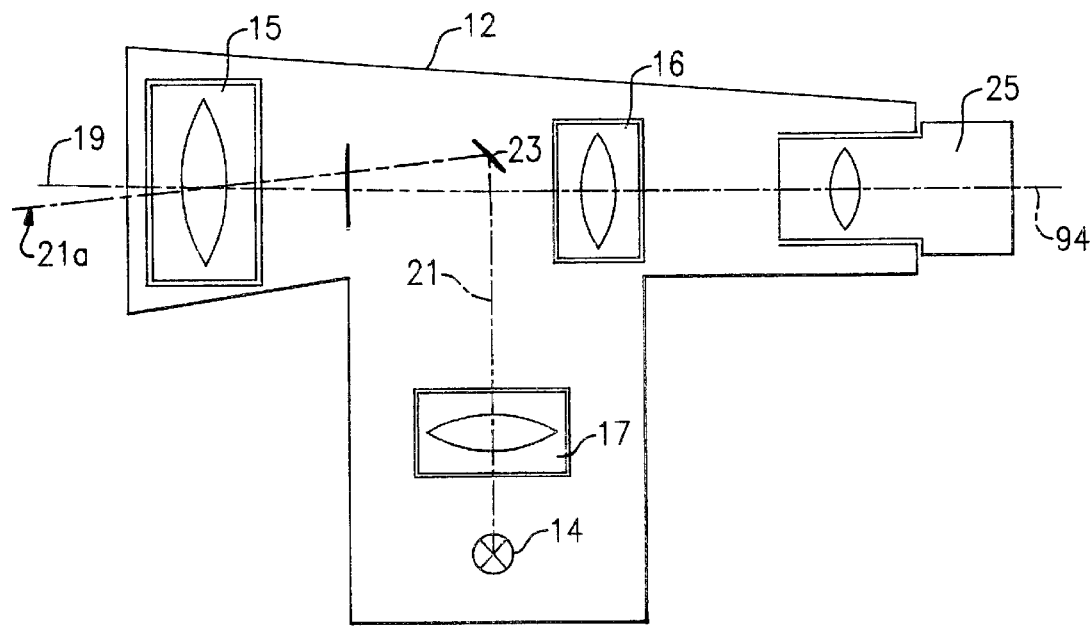
FIG. 2 is a physical schematic diagram of the interior of the optical instrument of FIG. 1.

The following description relates to a preferred embodiment of a focusing mechanism used in conjunction with an eyepiece of a small pupil indirect ophthalmoscope. It should be noted, however, that the described focusing mechanism can be used in conjunction with numerous optical instruments, including telescopes, cameras, and the like. Furthermore and throughout the course of discussion which follows, certain terms such as "front", "rear", "lateral", "top", and "bottom" are used. The use of these terms, however, is merely to provide a frame of reference with regard to the accompanying drawings and should not be construed to be overly limiting of the present invention. Prior to describing the focusing mechanism, reference is made to FIGS. 1–3 which generally illustrates an ophthalmoscope 10 within which a focusing mechanism 20 according to the present invention can be implemented. In general, the ophthalmoscope 10 herein described includes an instrument housing 12 supported by a hand-grippable battery handle 11, the housing having a number of optical components contained therein, including a light source 14 and three lens modules 15, 16, and 17. One of the lens modules is an objective lens module 15 positioned adjacent a target end 18 of the housing 12. A second imaging lens module 16 is aligned with the objective lens module 15 along an instrument optical axis 19 and an illumination lens module 17 is disposed between the latter two modules 15, 16 such that an illumination axis 21 of the instrument 10 extending from the light source 14 through the illumination lens module 17 passes through the optical axis 19. An angled mirror 23 disposed near the optical axis of the instrument receives the light from the light source 14 and causes the light to pass through the objective lens module 15 and to the target of interest (not shown) along the continuation of illumination axis 21a, FIG. 2. The position of the angled mirror 23 along the return light path, however, is offset relative to the optical axis 19 and hence is not imaged to a user at an eyepiece 25 positioned at a viewing end of the instrument housing 12.

Figure 3:
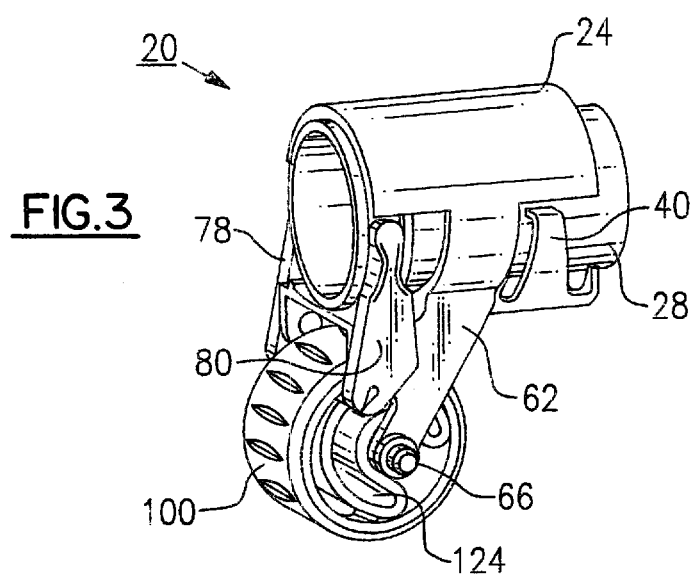
FIG. 3 is a side perspective view of a focusing mechanism according to a preferred embodiment of the present invention.
Figure 9:
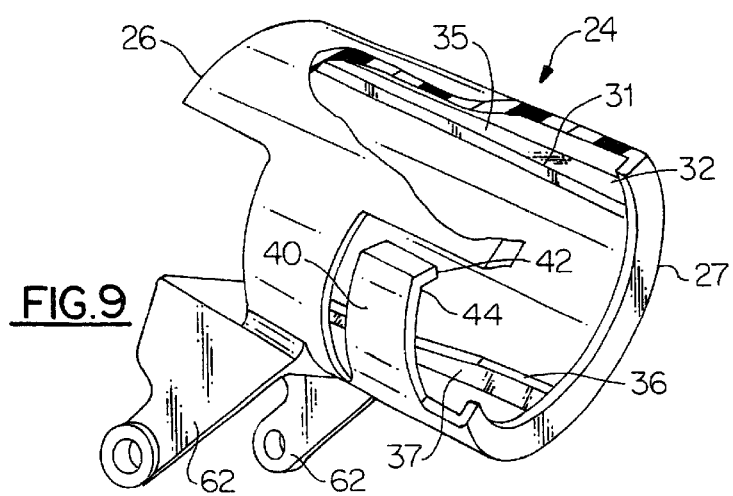
FIG. 9 is a top perspective view, partially cutaway, of the stationary carrier of the focusing mechanism of FIGS. 3–8.
Figure 4:
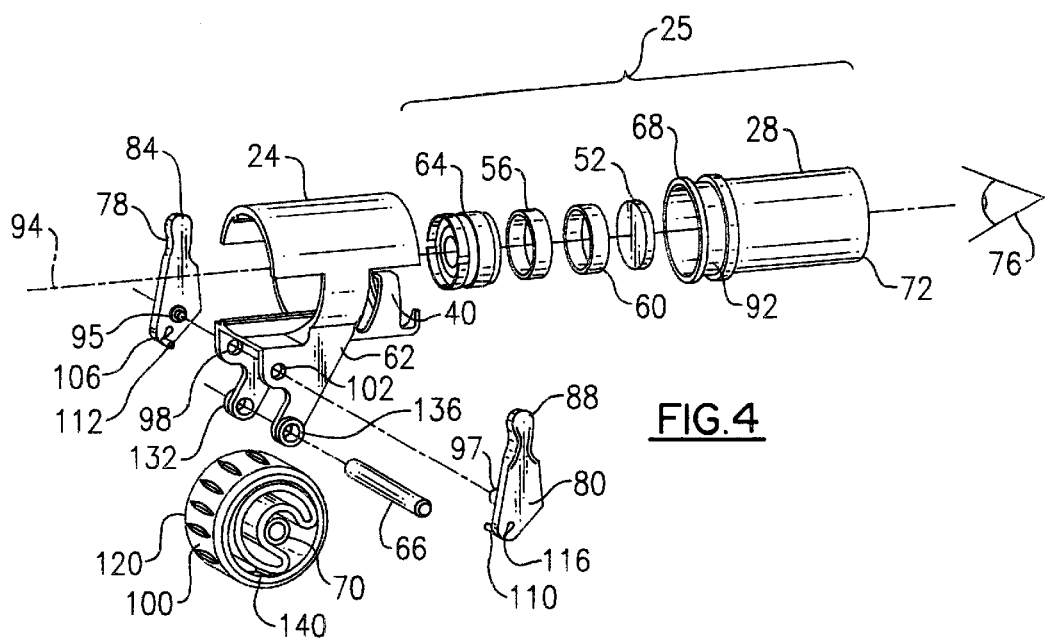
FIG. 4 is a side perspective exploded view of the focusing mechanism of FIG. 3.
Figure 5:
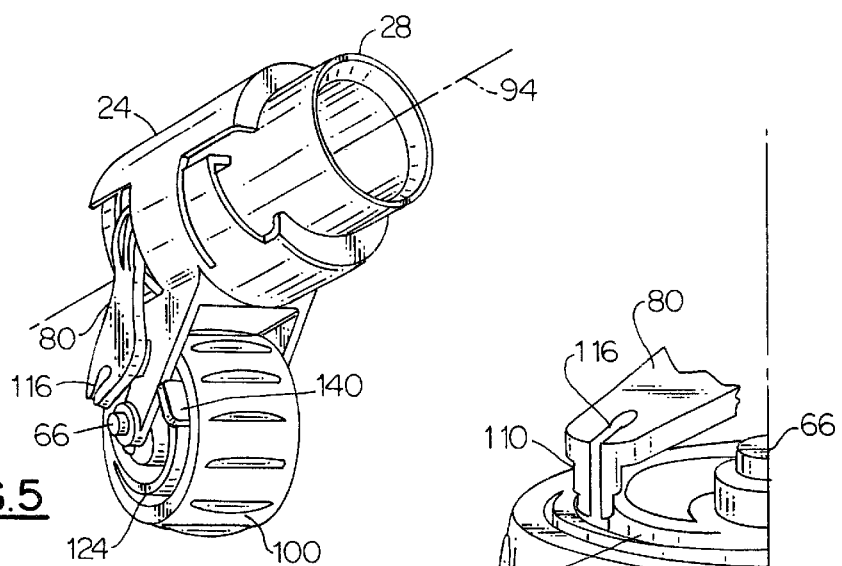
FIG. 5 is a rotated perspective view of the focusing mechanism of FIGS. 3 and 4.

Referring now to FIGS. 3 and 4, the focusing mechanism 20 according to the preferred embodiment includes an open-ended stationary carrier 24 which supports an eyepiece housing 28. Referring more specifically to FIGS. 3, 4, and 9, the stationary carrier 24 is defined by a substantially cylindrical configuration including respective distal and proximal ends 26, 27 and is preferably formed from an injection molded plastic. Two pairs of interior bearing surfaces 32, 36 are provided on each of the ends 31 (only one end being shown in FIG. 9) of a pair of parallel rails 35, 37 disposed on one side of the stationary carrier 24 on which the eyepiece housing 28 can slide during focusing thereof. The stationary carrier 24 further includes an integral spring finger 40 having a radial bearing surface 42 projecting at the unsupported end 44 thereof. The spring finger 40 provides a preload against the retained eyepiece housing in a radial direction such that the surface 42 pushes the eyepiece housing 28 against each of the pairs of interior bearing surfaces 32, 36. The above engagement assures the optical axis 94 of the eyepiece 25 remains aligned with the optical axis 19 of the instrument as the eyepiece is being focused.

Referring more particularly to the exploded FIG. 4, a pair of diopter lenses 52, 56 are provided within the confines of the eyepiece housing 28, the lenses being separated by a spacer 60. A lens retaining nut 64 added to the distal end 68 of the eyepiece housing 28 (that is, the side opposite to a viewing side 72 of the housing relative to a physician's eye 76) seals the above optical components.

The stationary carrier 24 further includes a pair of retaining legs 62, each of which are interconnected to a rotatable thumb wheel 100 through an axle 66 provided in a center opening 70 of the thumb wheel.

A pair of levers 78, 80, also preferably made from an injection molded plastic, but otherwise being made from any other suitable material, engage and push the eyepiece housing 28 along the optical axis for diopter correction (focusing). The top ends 84, 88 of the levers 78, 80 are located in a lever channel 92, which is provided at a distal end of the eyepiece housing 28, and contact the channel effectively on a diameter which passes through the optical axis 94 of the eyepiece 25. Such contact ensures that any forces of the levers 78, 80 on the eyepiece housing 28 will be effectively disposed in a direction which is along the optical axis 94.

The inwardly directed force applied to the eyepiece housing through the cantilevered spring finger 40 eliminates any radial free play between the eyepiece housing 28 and the stationary carrier 24. This spring finger 40 is preloaded radially against the eyepiece housing 28 and provides a constant radial load on the housing and also produces the "feel" of the mechanism. As a result, the optical axis 94 of the eyepiece 25 is maintained coincident with the optical axis 19 of the instrument 10, FIG. 2, throughout the extent of the travel of the eyepiece housing 28.

The two levers 78, 80 pivot via respective bosses 95, 97 that engage holes 98, 102 provided in the bottom of the stationary carrier 24. Extensions 106, 110 of the levers 78, 80 beneath the bosses 95, 97 terminate at split bosses 112, 116 that engage corresponding cam channels 120, 124 in the focusing thumb wheel 100. Identical spiral cam channels 120, 124 are provided on each side of the thumb wheel 100, with one cam channel 120 engaging the split boss 112 on the first lever 78 and the remaining cam channel 124 engaging the split boss 116 on the second lever 80.

Due to the split nature of the lever extensions 106, 110, the bosses 112, 116 on each lever 78, 80 contact both sides of the corresponding cam channel 120, 124 simultaneously; consequently, there is no radial free play between the levers 76, 80 and the rotatable thumb wheel 100. Therefore, rotational motion of the thumb wheel 100 results in radial motion of the split bosses 112, 116 on the levers 78, 80 relative to the thumb wheel 100. Preferably, and according to this embodiment the hinging axis and the axis defined by the thumb wheel axle 66; ie., the axis of rotation, are each perpendicular to the optical axis 94 of the eyepiece housing 28.

Figure 6:
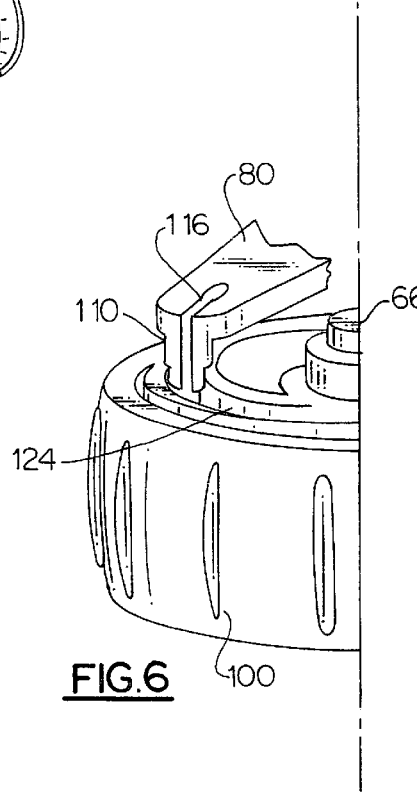
FIG. 6 is an enlarged partial view of the focusing mechanism of FIGS. 3–5 and more particularly depicts the engagement of the levers with the spiral cam channel of the rotatable thumb wheel.
Figure 7:
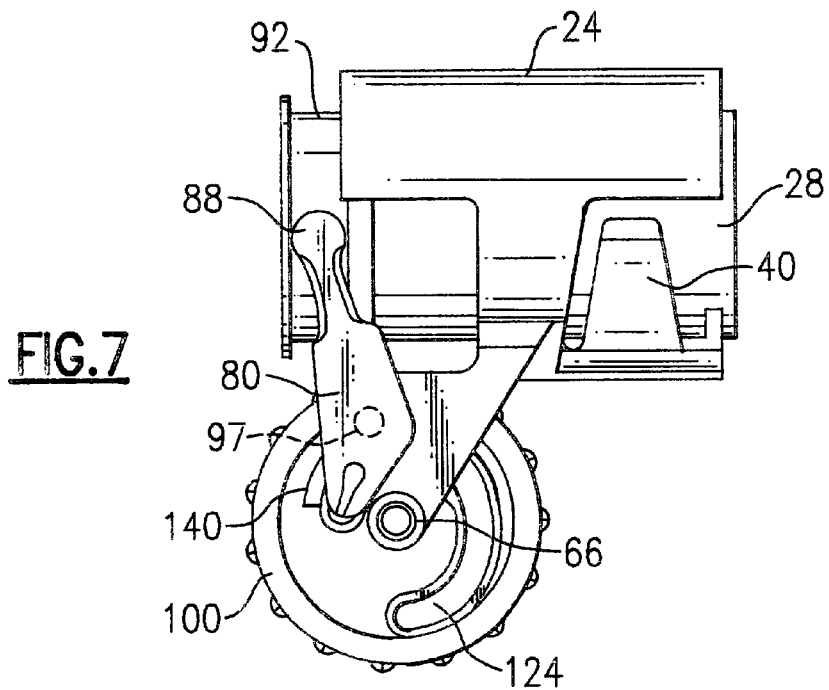
FIG. 7 is a side view of the stationary carrier of the focusing mechanism of FIGS. 3–5.
Figure 8:
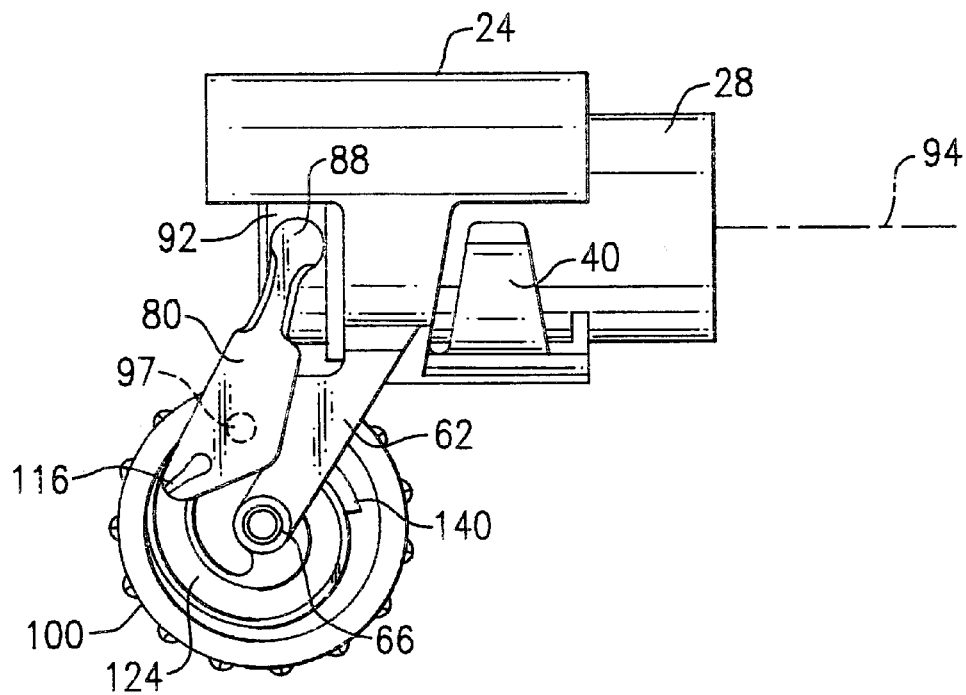
FIG. 8 is a side view of the focusing mechanism of FIGS. 3–5 illustrating the axial movement of a retained eyepiece following a predetermined amount of rotational movement of the thumb wheel.

The rotatable thumb wheel 100 rotates about the axle 66 passing through the center opening 70 of the thumb wheel and also through a pair of holes 132, 136 provided in the retaining legs 62 of the stationary carrier 24. The cam channels 120, 124 in the thumb wheel 100 are designed such that, when the thumb wheel rotates about the axle 66, the engaged split bosses 112, 116 move radially relative to the wheel, tracking the channels 120, 124, as shown in FIGS. 6–8. The pivoting action of the levers 78, 80 and the fixed relation between the stationary carrier 24 and the thumb wheel 100 therefore produces corresponding axial movement of the eyepiece housing 28. The degree of rotational motion of the thumb wheel 100 is controlled by stops 140 placed at ends of each of the cam channels 120, 124. Preferably, the stops 140 engage the retaining legs 62 of the stationary carrier 24 and not the levers 78, 80, further insuring that end of travel loads are not imparted to the levers 78, 80 or to the eyepiece housing 28. It will be readily apparent to those who now have an understanding of the principles of the present invention that the desired or appropriate ratio of eyepiece housing motion to thumb wheel rotation is achieved by proper sizing of the geometry of the cam channels, 120, 124, the levers 78, 80 and the stationary carrier 28. Over the course of axial movement of the eyepiece housing, the top ends 84, 88 of each of the levers 78, 80 remain substantially aligned with the optical axis 94 of the eyepiece 25.

Parts List for FIGS. 1–9

| | |
|---|---|
| 10 | ophthalmoscope |
| 11 | handle |
| 12 | instrument housing |
| 14 | light source |
| 15 | objective lens module |
| 16 | imaging lens module |
| 17 | illumination lens module |
| 18 | target end |
| 19 | optical axis of instrument |
| 20 | focusing mechanism |
| 21 | illumination axis |
| 21a | illumination axis |
| 23 | angled mirror |
| 24 | stationary carrier |
| 25 | eyepiece |
| 26 | distal end |
| 27 | proximal end |
| 28 | eyepiece housing |
| 31 | end |
| 32 | interior bearing surface |
| 35 | rail |
| 36 | bearing surface |
| 37 | rail |
| 40 | spring finger |
| 42 | bearing surface |
| 44 | end |
| 52 | diopter lens |
| 56 | diopter lens |
| 60 | spacer |
| 62 | retaining legs |
| 64 | lens retaining nut |
| 66 | axle |
| 68 | front side |
| 70 | center opening |
| 72 | viewing side |
| 76 | physician's eye |
| 78 | lever |
| 80 | lever |
| 84 | top end |
| 88 | top end |
| 92 | lever channel |
| 94 | optical axis of eyepiece |
| 95 | boss |
| 97 | boss |
| 98 | hole |
| 100 | rotatable thumb wheel |
| 102 | hole |
| 106 | extension |
| 110 | extension |
| 112 | split boss |
| 116 | split boss |
| 120 | cam channel |
| 124 | cam channel |
| 132 | hole |
| 136 | hole |
| 140 | stops |

Modifications and variations of the above-described embodiment are clearly possible which encompass the inventive concepts set forth herein. For example, the top ends of each of the levers can also include split bosses to provide simultaneous engagement with the lever channel 92. Such modifications and variations are clearly recognized as being covered though not specifically stated herein according to the following claims.

We claim:

1. A focusing mechanism comprising:
a eyepiece having at least one lens element retained within an eyepiece housing;
a stationary carrier for retaining said eyepiece;
a rotatable thumb wheel operatively connected to said stationary carrier; and
at least one lever operatively connecting said eyepiece housing and said thumb wheel, said thumb wheel including a cam channel for receiving a first end of said at least one lever, and in which an opposing second end of said at least one lever engages said eyepiece housing, such that rotational movement of said thumb wheel produces corresponding axial movement of the eyepiece relative to the stationary carrier.

2. A focusing mechanism as recited in claim 1, including means for radially biasing said eyepiece within said stationary carrier.

3. A focusing mechanism as recited in claim 2, wherein said biasing means includes at least one spring finger provided on a wall of said stationary carrier for radially biasing said eyepiece housing within said carrier.

4. A focusing mechanism as recited in claim 3, wherein said stationary carrier includes an interior surface having at least one guide surface for the eyepiece housing to track against during axial movement thereof.

5. A focusing mechanism as recited in claim 4, wherein said at least one spring finger biases said eyepiece housing into substantial contact with at least one guide surface.

6. A focusing mechanism as recited in claim 1, including a pair of levers operatively connecting said rotatable thumb wheel and said eyepiece housing, each of said levers being disposed on opposite sides of said thumb wheel, each said lever including a first end having follower means for engaging a corresponding cam channel wherein said cam channels are provided on opposite sides of said thumb wheel.

7. A focusing mechanism as recited in claim 6, wherein said eyepiece housing includes means for receiving the second end of each of said levers.

8. A focusing mechanism as recited in claim 7, wherein each of the second ends of said levers engage the eyepiece housing at substantially the centerline of said eyepiece housing.

9. A focusing mechanism as recited in claim 7, wherein each of the second ends of said levers are split to produce simultaneous engagement with the receiving means of said eyepiece housing.

10. A focusing mechanism as recited in claim 6, wherein each of the first ends of said levers is split to produce simultaneous engagement with each side of each cam channel of said thumb wheel.

11. A focusing mechanism as recited in claim 6, wherein each of said levers is hingably attached along a portion thereof to the stationary carrier.

12. A focusing mechanism as recited in claim 11, wherein the hinging attachment of said levers extends along a hinge axis, said hinge axis being substantially perpendicular to the optical axis of the eyepiece.

13. A focusing mechanism as recited in claim 1, wherein said at least one lever is hingably attached along a portion thereof to the stationary carrier.

14. A focusing mechanism as recited in claim 1, wherein said rotatable thumb wheel includes a stop provided at least one end of the cam channel.

15. A focusing mechanism as recited in claim 14, wherein said at least one stop engages said stationary carrier and does not engage either of said levers and said eyepiece during rotation of said thumb wheel.

16. An optical instrument comprising:
an instrument housing;
an eyepiece;
a stationary carrier disposed within said instrument housing and sized for retaining said eyepiece;
a rotatable thumb wheel operatively connected to said stationary carrier; and
at least one lever operatively connecting said eyepiece and said rotatable thumb wheel, said thumb wheel including a cam channel for receiving a first end of said at least one lever, and in which an opposing second end of said at least one lever engages said eyepiece such that rotational movement of said thumb wheel produces corresponding axial movement of the eyepiece relative to the stationary carrier.

17. An optical instrument as recited in claim 9, including means for radially biasing said eyepiece within said stationary carrier.

18. An optical instrument as recited in claim 17, wherein said biasing means includes at least one spring finger provided on a wall of said stationary carrier for radially biasing said eyepiece within said carrier.

19. An optical instrument as recited in claim 18, wherein said stationary carrier includes an interior surface having at least one guide surface for the eyepiece to track against during axial movement thereof.

20. An optical instrument as recited in claim 16, including a pair of levers operatively connecting said rotatable thumb wheel and said eyepiece, each of said levers being disposed on opposite sides of said rotatable thumb wheel, each said lever including a first end having follower means for engaging a corresponding cam channel wherein said cam channels are provided on opposite sides of said thumb wheel.

21. An optical instrument as recited in claim 20, wherein said eyepiece includes means for receiving the second end of each of said levers.

22. An optical instrument as recited in claim 21, wherein each of the second ends of said levers engage the eyepiece housing at substantially the centerline of said housing.

23. An optical instrument as recited in claim 21, wherein each of the second ends of said levers are split to produce simultaneous engagement with the receiving means of said eyepiece housing.

24. An optical instrument as recited in claim 20, wherein each of the first ends of said levers is split to produce simultaneous engagement with each side of each cam channel of said thumb wheel.

25. An optical instrument as recited in claim 16, wherein said at least one lever is hingably attached along a portion thereof to the stationary carrier.

26. An optical instrument as recited in claim 20, wherein each of said levers is hingably attached along a portion thereof to the stationary carrier.

27. An optical instrument as recited in claim 26, wherein the hinging attachment of said levers extends along a hinge axis, said hinge axis being substantially perpendicular to the optical axis of the eyepiece.

28. An optical instrument as recited in claim 19, wherein said at least one spring finger biases said eyepiece into substantial contact with at least one guide surface.

29. An optical instrument as recited in claim 16, wherein said rotatable thumb wheel includes a stop provided at least one end of the cam channel.

30. An optical instrument as recited in claim 29, wherein said at least one stop engages said stationary carrier and does not engage either of said levers and said eyepiece during rotation of said thumb wheel.

31. An optical instrument as recited in claim 16, wherein said instrument is an ophthalmoscope.

32. A method of axially adjusting an eyepiece of an optical instrument along an optical axis of said instrument, said method comprising the steps of:

retaining an eyepiece housing in a stationary carrier, said stationary carrier being operatively connected to a rotatable thumb wheel;

linking a first end of at least one lever to said rotatable thumb wheel and a second end of said at least one lever to said eyepiece housing, said at least one lever being hingably attached to said stationary carrier; and rotating said rotatable thumb wheel, causing the first end of said at least one lever to track a spiral channel of said thumb wheel, pivoting said at least one lever about the hingable attachment to said stationary carrier to produce axial movement of said eyepiece.

33. A method as recited in claim 32, including the steps of providing a pair of levers, each of said levers including a split boss at least at the first end thereof to provide simultaneous engagement with sides of corresponding spiral channels provided on opposite sides of said thumb wheel during rotation thereof.

34. A method as recited in claim 33, including the step of engaging the second end of each of said levers at substantially the centerline of said eyepiece housing.

35. A method as recited in claim 33, including the step of providing stops at the ends of each spiral channel, said stops being disposed to engage said stationary carrier and not said levers when an end of travel is reached during said rotating step.

* * * * *